United States Patent [19]

Horie et al.

[11] 4,403,025
[45] Sep. 6, 1983

[54] ELECTROPHOTOGRAPHIC PHOTORECEPTOR

[75] Inventors: Seiji Horie; Masayoshi Nagata; Junji Nakano; Hideo Sato, all of Asaka, Japan

[73] Assignee: Fuji Photo Film Co., Ltd., Kanagawa, Japan

[21] Appl. No.: 276,745

[22] Filed: Jun. 24, 1981

[30] Foreign Application Priority Data

Jun. 24, 1980 [JP] Japan .................. 55/85495

[51] Int. Cl.³ ............................................. G03G 5/04
[52] U.S. Cl. ...................................... 430/59; 430/73; 430/74; 430/76; 430/77
[58] Field of Search ............... 430/58, 59, 73, 76, 430/77, 74; 564/251

[56] References Cited

U.S. PATENT DOCUMENTS

| | | | |
|---|---|---|---|
| 3,066,023 | 11/1962 | Schlesinger | 430/73 |
| 3,717,462 | 2/1973 | Negishi et al. | 430/73 |
| 4,150,987 | 4/1979 | Anderson et al. | 430/58 |
| 4,278,747 | 7/1981 | Murayama et al. | 430/73 |
| 4,297,426 | 10/1981 | Sakai et al. | 430/58 |

*Primary Examiner*—Richard L. Schilling
*Attorney, Agent, or Firm*—Sughrue, Mion, Zinn, Macpeak and Seas

[57] ABSTRACT

An electrophotographic photoreceptor is described comprising an N-arylamino substituted hydrazone compound represented by formula (I), (II), or (III), in a light-sensitive layer thereof provided on a conductive support; formulae (I), (II), and (III) are as follows:

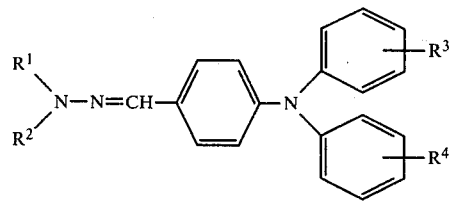

(I)

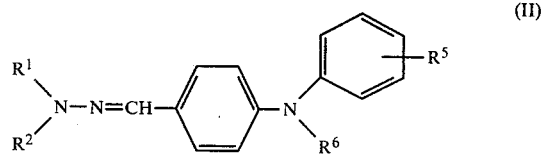

(II)

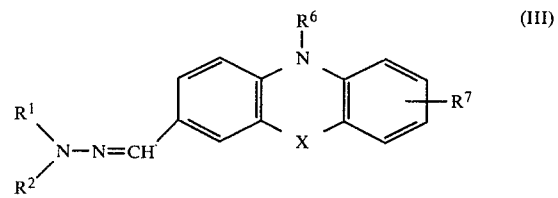

(III)

wherein X represents O, S or N—$R^6$; $R^1$ and $R^2$ each represents a non-substituted or a substituted straight or branched chain alkyl group containing from 1 to 12 carbon atoms, a non-substituted or a substituted straight or branched chain aralkyl group containing from 7 to 20 carbon atoms, or a non-substituted or a substituted aryl group, the aryl group including monovalent residues of monocyclic aromatic rings and condensed polycyclic aromatic rings having from 2 to 4 rings therein; $R^3$, $R^4$, $R^5$, and $R^7$ each represents hydrogen, a non-substituted or a substituted straight or branched chain alkyl group containing from 1 to 12 carbon atoms, a non-substituted or a substituted straight or branched chain aralkyl group containing from 7 to 20 carbon atoms, a straight or a branched chain alkoxy group containing from 1 to 4 carbon atoms, an aryloxy group containing from 6 to 10 carbon atoms, an acyl group containing from 2 to 8 carbon atoms, an alkoxycarbonyl group containing from 2 to 5 carbon atoms, a halogen atom, a nitro group, a monoalkylamino group whose alkyl moiety contains from 1 to 4 carbon atoms, a dialkylamino group whose alkyl moiety contains from 1 to 4 carbon atoms, or an amido group containing from 2 to 8 carbon atoms; and $R^6$ represents a non-substituted or a substituted straight or branched chain alkyl group containing from 1 to 12 carbon atoms, or a non-substituted or a substituted straight or branched chain aralkyl group containing from 1 to 12 carbon atoms.

10 Claims, 6 Drawing Figures

ELECTROPHOTOGRAPHIC PHOTORECEPTOR

FIELD OF THE INVENTION

This invention relates to an electrophotographic photoreceptor, and, more particularly, to an electrophotographic photoreceptor which contains a hydrazone compound in a light-sensitive layer formed on a conductive support.

BACKGROUND OF THE INVENTION

Materials which have been employed as the photoconductive materials of photoreceptors used in electrophotography include inorganic substances such as selenium, cadmium sulfide, zinc oxide, and the like.

The process of xerography, as disclosed by Carlson in U.S. Pat. No. 2,297,691, utilizes a photoconductive material comprising a support coated with a substance which can change its electric resistance depending upon the quantity of exposure which it receives during imagewise irradiation exposure, and which acts as an insulator under dark. In such a process, the photoconductive material is placed in the dark for an appropriate period of time for the purpose of dark adaptation, and then a uniform potential is created on its surface in the dark by a source of charge. Next, it is exposed to some form of irradiation having a pattern which possesses such an effect that the surface charge may be diminished, depending upon relative energy borne by each part of the pattern. The thus remaining surface charge or electrostatic latent image on the surface of the light-sensitive layer is converted into visible image by contact with an appropriate charge detecting and developing substance. Such a developing substance, referred to as a "toner", whether it is contained in an insulating liquid or in dry carrier, can adhere to the surface of the light-sensitive layer according to the electric charge pattern existing there. The toner attached to the electric charge pattern can be fixed thereon using known means, such as heat and/or pressure, or solvent vapors. On the other hand, it can be transferred onto a second support (e.g., paper, film, etc.). Similarly, it is possible to transfer the electrostatic latent image onto a second support and to develop it on the second support.

The process of xerography, wherein image is formed in such a manner as described above, is one basic type of imaging process. Fundamental characteristics required for photoreceptors in the electrophotography of this kind are as follows:

(1) The photoreceptor can be charged to create an appropriate value of potential in the dark.

(2) Leakage of charges created on the surface of a photoreceptor occurs in the dark only to a small extent.

(3) Selective discharging of the created charges takes place rapidly upon exposure to a pattern of light.

Conventionally used inorganic substances as described above have many advantages and at the same time, have various disadvantages. For instance, although selenium, which has so far been prevailingly used as a photoconductor, fully satisfies the above-described requirements (1) to (3), selenium photoreceptors suffer the disadvantages that (1) conditions for the production thereof are difficult to control, and therefore the production costs are high, (2) it lacks flexibility, and thus to shape it in a belt-form is difficult, and (3) it must be handled with great care because it is very sensitive to heat and mechanical impact. Cadmium sulfide and zinc oxide are each used for the production of photoreceptor in the form of dispersion in a resin binder. However, photoreceptors of this type do not well withstand repeated uses, due to mechanical deficiencies in smoothness, hardness, tensile strength, abrasion-resisting properties, and so forth.

In recent years, electrophotographic photoreceptors utilizing various organic substances have been proposed with the intention of overcoming the aforementioned defects inherent in the inorganic substances. At present some of these photoreceptors are put to practical use. For example, there is a photoreceptor comprising poly-N-vinylcarbazole and 2,4,7-trinitrofluorene-9-one (U.S. Pat. No. 3,484,237), a photoreceptor in which poly-N-vinylcarbazole is sensitized with a pyrylium salt series dye (published examined Japanese Patent Application No. 25658/73), a photoreceptor containing an organic pigment as a main component (Japanese Patent Application (OPI) No. 37543/72 (the term "OPI" as used herein refers to a "published unexamined Japanese patent application")), a photoreceptor containing an eutectic complex of a dye and a resin as a main component (Japanese Patent Application (OPI) No. 10735/72) and so on. These photoreceptors have excellent characteristics and seem to be worthy of practical uses. However, taking into account various requirements for photoreceptors useful for electrophotography, fully satisfactory photoreceptors have not yet been obtained. Although the properties required for an excellent photoreceptor depend to some extent upon the end use thereof and the method employed for the production thereof, the use of an excellent photoconductive substance is generally the key to the production of photoreceptors possessing excellent characteristics.

Photoreceptors which utilize hydrazone compounds as photoconductive substances are described, for example, in U.S. Pat. No. 3,717,462, which corresponds to published examined Japanese Patent Application No. 8137/73, Japanese Patent Application (OPI) No. 59143/79, which corresponds to U.S. Pat. No. 4,150,987, Japanese Patent Application (OPI) Nos. 52063/80, 52064/80, and so on. In each of these cases, condensed polycyclic compounds or N-alkylamino substituted compounds of hydrazone are employed. However, these compounds have insufficient stabilities to oxidation with ozone generated by corona charging, light and heat, and unsatisfactory dark decay characteristics, and so on.

The hydrazone compounds having carbazole rings as described in Japanese Patent Application (OPI) No. 46760/80 are improved in their stability and dark decay characteristics to a considerable extent. However, the improvements in the stability and the dark decay characteristics are still insufficient, and, furthermore, these carbazole compounds suffer a serious disadvantage in that it is hard to obtain pure compounds because of difficulties in synthesizing them, and therefore production costs are very high.

SUMMARY OF THE INVENTION

Bearing in mind the foregoing, it is an object of this invention to provide electrophotographic photoreceptors which utilize photoconductive substances exhibiting further improved properties.

We have now found that particular hydrazone compounds having the formulae (I) to (III) illustrated hereinafter function efficiently as a photoconductive substance for the electrophotographic photoreceptor and exhibit excellent properties as a charge carrier transport substance.

In accordance with this invention, it has been found that the use of N-arylamino substituted hydrazone compounds as a photoconductive substance in the electrophotographic photoreceptor improves (1) stability to oxidation due to ozone generated by corona charging, light and heat, and (2) dark decay characteristics, and further, raises sensitivity, reduces residual potential which causes fog, reduces variations of residual potential and sensitivity which result from repeated uses, and confers excellent durability upon the photoreceptor. In addition, the hydrazone compounds of this invention can be relatively easily obtained in a pure state, and therefore can be produced at a low price.

More specifically, the above-described object of this invention is attained with an electrophotographic photoreceptor which has a light-sensitive layer containing a hydrazone compound represented by formula (I), (II) or (III):

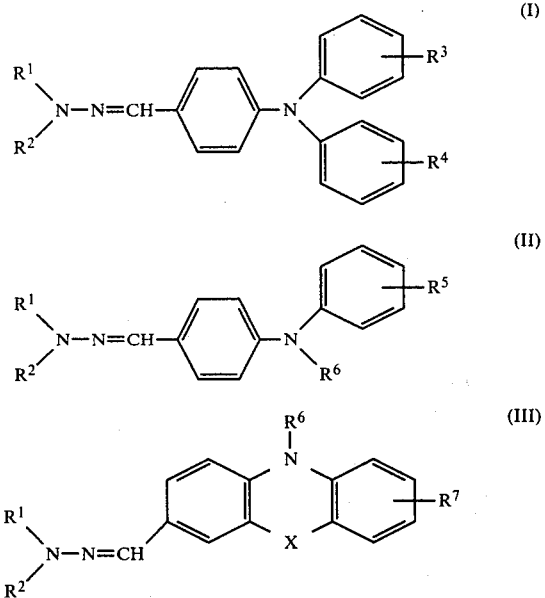

wherein X represents O, S or >N—R⁶; R¹ and R² each represents a non-substituted or a substituted straight or branched chain alkyl group containing from 1 to 12 carbon atoms, a non-substituted or a substituted straight or branched chain aralkyl group containing from 7 to 20 carbon atoms, or a non-substituted or a substituted aryl group, the aryl group including monovalent residues of monocyclic aromatic rings and those of condensed polycyclic aromatic rings having from 2 to 4 rings (wherein R¹ and R² may be the same as or different from each other); R³, R⁴, R⁵ and R⁷ each represents hydrogen, a non-substituted or a substituted straight or branched chain alkyl group containing from 1 to 12 carbon atoms, a non-substituted or a substituted straight or branched chain aralkyl group containing from 7 to 20 carbon atoms, a straight or a branched chain alkoxy group containing from 1 to 4 carbon atoms, an aryloxy group containing from 6 to 10 carbon atoms, an acyl group containing from 2 to 8 carbon atoms, an alkoxycarbonyl group containing from 2 to 5 carbon atoms, a halogen atom, a nitro group, a monoalkylamino group substituted with an alkyl group containing from 1 to 4 carbon atoms, a dialkylamino group substituted with alkyl groups containing from 1 to 4 carbon atoms, or an amido group containing from 2 to 8 carbon atoms; and R⁶ represents a non-substituted or a substituted straight or branched chain alkyl group containing from 1 to 12 carbon atoms, or a non-substituted or a substituted straight or branched chain aralkyl group containing from 1 to 12 carbon atoms.

In the case wherein R¹, R², R³, R⁴, R⁵, R⁶, or R⁷ has a substituent group, the substituent group is preferably a halogen atom, an alkoxy group, an aryloxy group, a dialkylamino group or an alkylthio group. In the case wherein R¹ or R² represents an aryl group, the substituent group further may be an alkyl group in addition to the above-described groups.

DETAILED DESCRIPTION OF THE INVENTION

Figure 1:
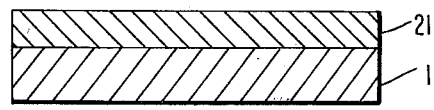
FIGS. 1 to 4 are schematic cross-sections of electrophotographic photoreceptors of this invention.

In the formulae (I), (II) and (III), X represents O, S or >N—R⁶; R¹ and R² each represents a non-substituted or a substituted straight or branched chain alkyl group containing from 1 to 12 carbon atoms, a non-substituted or a substituted straight or branched chain aralkyl group containing from 7 to 20 carbon atoms, or a non-substituted or a substituted aryl group, the aryl group including monovalent residues of monocyclic aromatic rings and those of condensed polycyclic aromatic rings having from 2 to 4 rings (wherein R¹ and R² may be the same as or different from each other); R³, R⁴, R⁵ and R⁷ each represents hydrogen, a non-substituted or a substituted straight or branched chain alkyl group containing from 1 to 12 carbon atoms, a non-substituted or a substituted straight or branched chain aralkyl group containing from 7 to 20 carbon atoms, a straight or a branched chain alkoxy group containing from 1 to 4 carbon atoms, an aryloxy group containing from 6 to 10 carbon atoms, an acyl group containing from 2 to 8 carbon atoms, an alkoxycarbonyl group containing from 2 to 5 carbon atoms, a halogen atom, a nitro group, a monoalkylamino group substituted with an alkyl group containing from 1 to 4 carbon atoms, a dialkylamino group substituted with alkyl groups containing from 1 to 4 carbon atoms, or an amido group containing from 2 to 8 carbon atoms; and R⁶ represents a non-substituted or a substituted straight or branched chain alkyl group containing from 1 to 12 carbon atoms, or a non-substituted or a substituted straight or branched chain aralkyl group containing from 1 to 12 carbon atoms.

In the case wherein R¹, R², R³, R⁴, R⁵, R⁶, or R⁷ has a substituent group, the substituent group is preferably a halogen atom, an alkoxy group, an aryloxy group, a dialkylamino group or an alkylthio group. In the case wherein R¹ or R² represents an aryl group, the substituent group further may be an alkyl group in addition to the above-described groups.

In the case wherein $R^1$ or $R^2$ is non-substituted alkyl groups, specific examples thereof include the methyl group, ethyl group, propyl group, butyl group, pentyl group, hexyl group, octyl group, nonyl group, dodecyl group, isopropyl group, isobutyl group, isopentyl group, 4-methylpentyl group, sec-butyl group and tert-butyl group. When $R^1$ or $R^2$ is an alkyl group having a substituent group, specific examples of the substituent group include chlorine, bromine, or fluorine as a halogen atom; a methoxy group, ethoxy group, propoxy group, butoxy group, or pentyloxy group as an alkoxy group; a phenoxy group, o-tolyloxy group, m-tolyloxy group, p-tolyloxy group, 1-naphthyloxy group, or 2-naphthyloxy group as an aryloxy group; a dimethylamino group, diethylamino group, dipropylamino group, N-methyl-N-ethylamino group, N-ethyl-N-propylamino group, or N-methyl-N-propylamino group as a dialkylamino group; and a methylthio group, ethylthio group, and propylthio group as an alkylthio group. The alkyl groups wherein at least any one of these substituent groups is attached to at least one carbon atom composing the alkyl group in an arbitrary position of its chain moiety include examples of the aforementioned alkyl groups for $R^1$ or $R^2$.

In the case wherein $R^1$ or $R^2$ is a non-substituted aralkyl group, specific examples thereof include a benzyl group, phenethyl group, 1-naphthylmethyl group, 2-naphthylmethyl group, 1-anthrylmethyl group and benzhydryl group. Examples of such substituent groups for the aralkyl group include the same groups as described in the case of the aforementioned alkyl groups for $R^1$ and $R^2$. As examples of the aralkyl group having a substituent group, mention may be made of the above-described aralkyl groups which each has in an arbitrary position of its nucleus or chain moiety at least one carbon atom to which at least any one of these substituent groups is attached.

When $R^1$ or $R^2$ is a non-substituted aryl group, specific examples thereof include a phenyl group, 1-naphthyl group, 2-naphthyl group, anthryl group, pyrenyl group, acenaphthenyl group and fluorenyl group. When $R^1$ or $R^2$ is an aryl group having a substituent group, specific examples of the substituent group include alkyl groups, such as a methyl group, ethyl group, propyl group, butyl group, pentyl group, isopropyl group, isobutyl group, and isopentyl group, in addition to the substituent groups described as specific examples in the case of the aforementioned alkyl groups. The aryl groups wherein at least any one of these substituent groups is attached to at least one carbon atom composing the aryl groups in an arbitrary position of its chain moiety include examples of the aforementioned aryl groups for $R^1$ or $R^2$.

Preferable combinations of two groups representing $R^1$ and $R^2$, respectively, include the cases wherein one is phenyl group and the other is methyl group, ethyl group, benzyl group, or phenyl group.

In the case wherein $R^3$, $R^4$, $R^5$, or $R^7$ is a non-substituted alkyl group or a non-substituted aralkyl group, specific examples thereof include the same groups described as specific examples in the case of the aforementioned non-substituted alkyl or aralkyl groups represented by $R^1$ or $R^2$, respectively. When $R^3$, $R^4$, $R^5$, or $R^7$ is an alkyl or an aralkyl group having substituent group(s), specific examples of the substituent group include the same groups described above for $R^1$ and $R^2$. The alkyl groups or aralkyl groups wherein at least any one of these substituent groups is attached to at least one carbon atom of the alkyl groups or aralkyl groups include the aforementioned alkyl groups or aralkyl groups for $R^3$, $R^4$, $R^5$, or $R^7$.

When $R^3$, $R^4$, $R^5$, or $R^7$ represents a straight or a branched chain alkoxy group containing from 1 to 4 carbon atoms, specific examples thereof include methoxy group, ethoxy group, propoxy group, butoxy group, isopropoxy group and sec-butoxy group. When $R^3$, $R^4$, $R^5$, or $R^7$ represents an aryloxy group, specific examples thereof include phenoxy group, o-tolyloxy group, m-tolyloxy group and p-tolyloxy group. when $R^3$, $R^4$, $R^5$, or $R^7$ represents an acyl group, specific examples thereof include an acetyl group, propionyl group, benzoyl group, o-toluoyl group, m-toluoyl group and p-toluoyl group. when $R^3$, $R^4$, $R^5$, or $R^7$ represents an alkoxycarbonyl group containing from 2 to 5 carbon atoms, specific examples thereof include a methoxycarbonyl group, ethoxycarbonyl group, propoxycarbonyl group, and butoxycarbonyl group. When $R^3$, $R^4$, $R^5$, or $R^7$ represents a halogen atom, specific examples thereof include a chlorine atom, bromine atom, and fluorine atom. When $R^3$, $R^4$, $R^5$, or $R^7$ represents a monoalkylamino group whose alkyl moiety contains from 1 to 4 carbon atoms, specific examples thereof include a methylamino group, ethylamino group and butylamino group. When $R^3$, $R^4$, $R^5$, or $R^7$ represents a dialkylamino group whose alkyl moieties each contain from 1 to 4 carbon atoms, specific examples thereof include a dimethylamino group, diethylamino group, dipropylamino group, dibutylamino group, and N-methyl-N-ethylamino group. When $R^3$, $R^4$, $R^5$, or $R^7$ represents an amido group, specific examples thereof include acetamido group and propionamido group.

Preferable groups represented by $R^3$, $R^4$, $R^5$, or $R^7$ are hydrogen, a methyl group, and a methoxy group.

Specific examples of $R^6$ include the same non-substituted alkyl groups, substituted alkyl groups, non-substituted aralkyl groups and substituted aralkyl groups as those described for $R^1$. Preferable examples of $R^6$ are a methyl group and an ethyl group.

Specific examples of hydrazone compounds represented by formulae (I) to (III) are illustrated below:

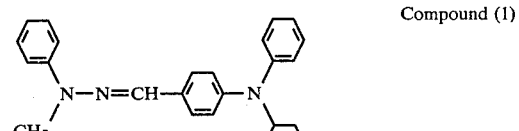

Compound (1)

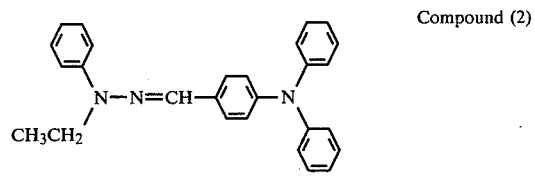

Compound (2)

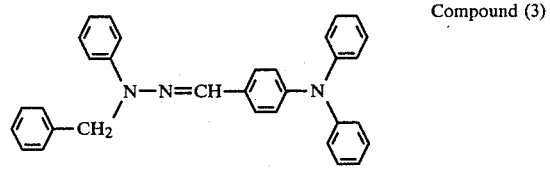

Compound (3)

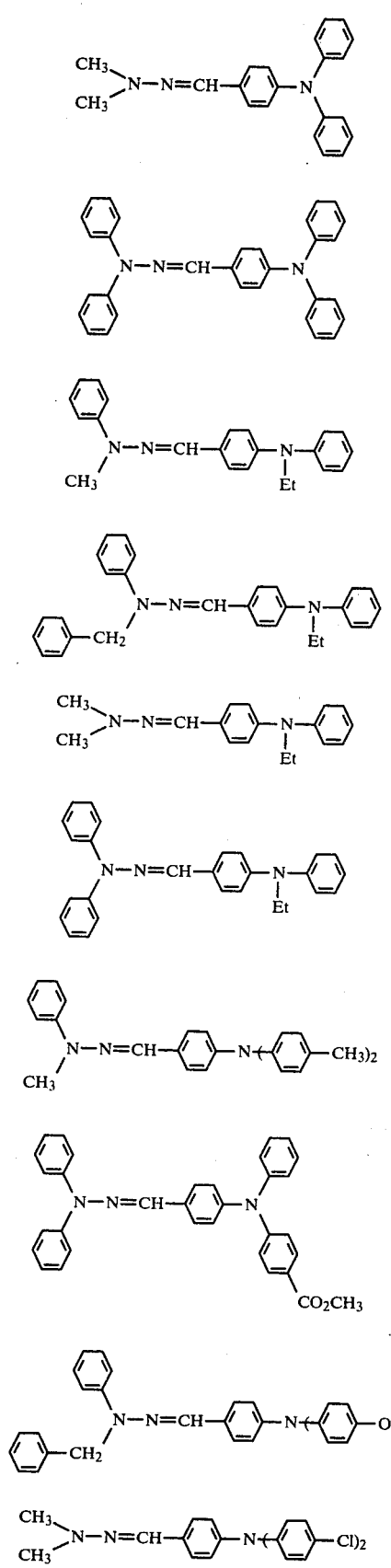
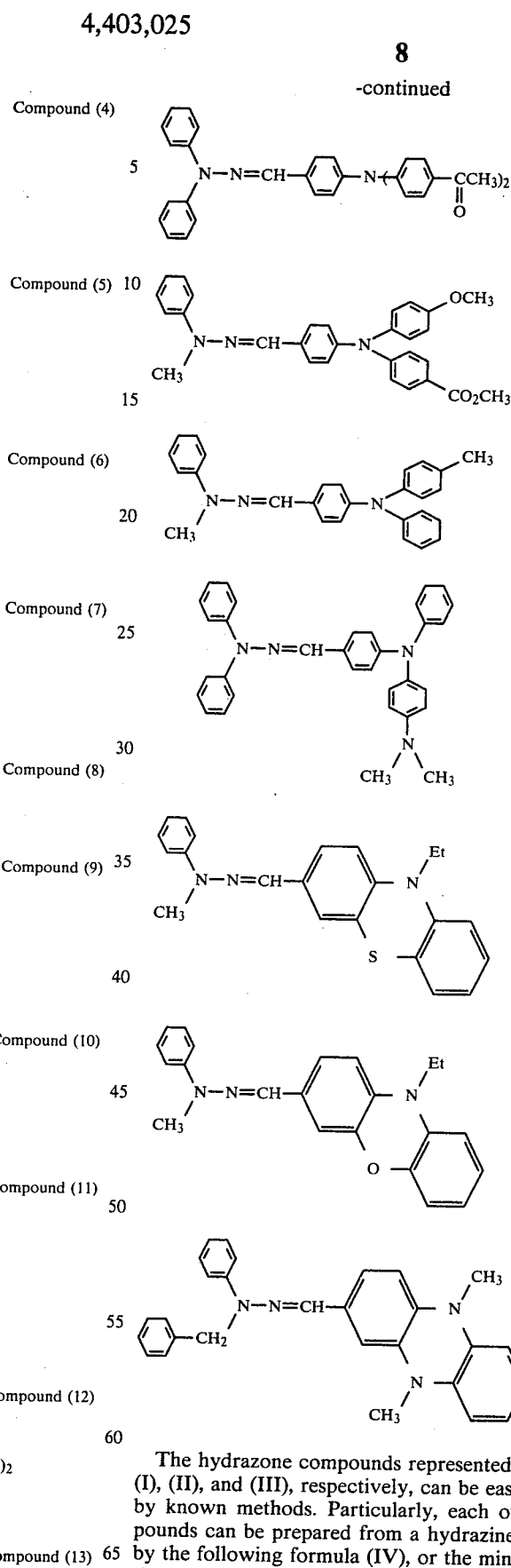

The hydrazone compounds represented by formulae (I), (II), and (III), respectively, can be easily produced by known methods. Particularly, each of these compounds can be prepared from a hydrazine represented by the following formula (IV), or the mineral acid salt thereof, and an arylaldehyde represented by the formula (V), (VI), or (VII) by adding thereto a small amount of acid (such as glacial acetic acid or an inorganic acid) as a condensing agent, if necessary, and by allowing them to undergo the condensation reaction in a solvent in a conventional manner. As the solvent, alcohols such as methanol, ethanol, and the like, tetrahydrofuran, acetic acid, etc., can be used, independently or in the form of mixture thereof.

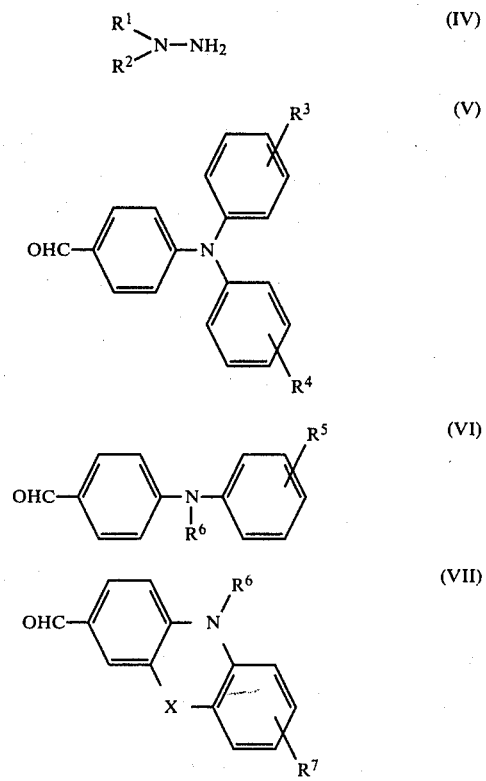

In the formulae (IV) through (VII), X represents —O—, —S— or NR$^6$, and R$^1$ through R$^7$ have the same meanings as R$^1$ through R$^7$ in the formulae (I), (II), and (III).

Each of the aldehyde compounds represented by the above-described general formulae (V), (VI) and (VII) can be easily obtained according to the known Vilsmeier's method (described in *Ber.*, Vol. 60, p. 119 (1927)), in which an aromatic amine compound and a heterocyclic compound are added to the Vilsmeier's reagent (which is prepared from phosphorus oxychloride and N,N-dimethylformamide) at a low temperature, and the thus obtained reaction product is subjected to hydrolysis to obtain the intended compound.

SYNTHESIS EXAMPLE

Synthesis of Compound (1)

A Vilsmeier's reagent was prepared by adding dropwise phosphoryl trichloride (POCl$_3$) (46 g) to N,N-dimethylformamide (22 g) with stirring in an ice bath. Thereto there was added a solution (200 ml) of N,N,N-triphenylamine (50 g) in N,N-dimethylformamide while continuing cooling in the ice bath. The stirring was continued for about one hour, and then the bath temperature was raised to about 90° C. While maintaining that temperature, the stirring was continued further for two hours. At the conclusion of the reaction the reaction system was cooled to room temperature, and then the reaction product was poured into ice water. The thus obtained aqueous solution was neutralized with an alkali to separate out a yellow precipitate. The precipitate was filtered off, dried and then recrystallized from ethyl alcohol. Thus, p-(N,N-diphenylamino)benzaldehyde (43 g) was obtained.

The above-described aldehyde (3.35 g) and N-methyl-N-phenylhydrazine (1.5 g) were dissolved in ethanol (50 ml), refluxed for about one hour, and then cooled by allowing it to stand at room temperature. Thereupon, a yellow precipitate was separated out. The precipitate was filtered off, dried and recrystallized from ethanol and a small amount of benzene. Thus, p-(N,N-diphenylamino)benzaldehyde N'-methyl-N'-phenylhydrazone (Compound (1)) (3.3 g) was obtained. m.p. 144.5°–146.5° C.

Other compounds were prepared from corresponding hydrazines and aldehydes in the same manner as described above. Compound examples and their melting points are set forth below:

| | Melting Point |
|---|---|
| Compound (3) | 176–177° C. |
| Compound (4) | 97–98.5° C. |
| Compound (5) | 158–159.5° C. |
| Compound (6) | 160–162° C. |
| Compound (18) | 139–141° C. |

The photoreceptors of this invention contain the hydrazone compounds such as those illustrated above. Each of these hydrazone compounds can be employed in any of the embodiments as are illustrated in FIGS. 1 to 4.

A photoreceptor as shown in FIG. 1 is constructed of a conductive support 1 and a light-sensitive layer 21 provided thereon, which layer 21 comprises a hydrazone compound of this invention, a sensitizing dye, and a binder (resin).

Figure 2:
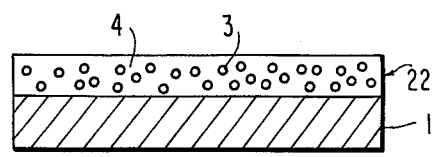

A photoreceptor as shown in FIG. 2 is constructed of a conductive support 1 and a light-sensitive layer 22 provided thereon, in which layer 22 a charge generating substance 3 is dispersed in a charge transport medium 4 comprising the hydrazone compound of this invention and a binder.

Figure 3:
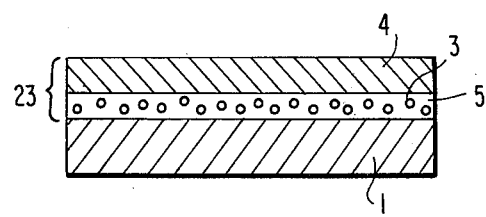

A photoreceptor as shown in FIG. 3 is constructed of a conductive support 1, a charge generating layer 5 containing a charge generating substance 3 as a main component, and a charge transport layer 4 containing the hydrazone compound of this invention, arranged in that order. Therein, the layer 5 and the layer 4 together constitute a light-sensitive layer 23.

Figure 4:
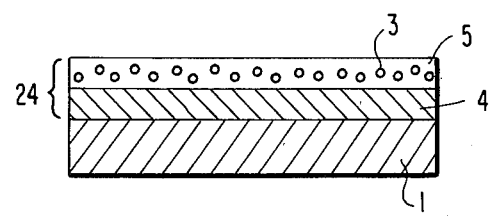

A photoreceptor as shown in FIG. 4 is constructed of a conductive support 1, a charge transport layer 4 containing the hydrazone compound of this invention and a charge generating layer 5 containing a charge generating substance 3 as a main component, arranged in that order. Therein, the layer 4 and the layer 5 constitute a light-sensitive layer 24.

In the photoreceptor of FIG. 1, the hydrazone compound functions as a photoconductive substance, and generation and transport of charge carrier indispensable for photo-induced discharge are carried out through the hydrazone compound. However, the hydrazone compound little absorbs light in the visible region and therefore it is necessary to sensitize the hydrazone compound by adding a sensitizing dye which can absorb light in the visible region to the light-sensitive layer for the purpose of formation of image using visible rays.

In the case of the photoreceptor of FIG. 2, the hydrazone compound constitutes a charge transport medium together with a binder (or with a binder and a plasticizer) and, on the other hand, charge is generated by a charge generating substance, such as inorganic or organic pigment. In this instance the charge transport medium should possess such abilities as to accept charge generated mainly by the charge generating substance and to transport the charge. To this case is attached one basic condition, viz., that the absorption spectrum of the charge generating substance must not have, particularly in the visible region, any overlap with that of the hydrazone compound. This is because the efficient generation of charge by the charge generating substance necessitates the transmission of light by the medium and the arrival of light at the surface of the charge generating substance. The hydrazone compounds of this invention scarcely absorb light in the visible region, and therefore they exhibit their effectiveness as a charge transport substance when used in combination with charge generating substances which can generally absorb visible rays and generate charges.

In the photoreceptor of FIG. 3, light transmitted by the charge transport layer 4 reaches to the charge generating layer 5 and in the area at which transmitted light arrives, generation of charge takes place. The generated charge is injected into the charge transport layer. The charge transport layer accepts the injected charge and transports it. The apparent mechanism is that the generation of charge essential to the photo-induced discharge is conducted in the charge generating substance, and the function of charge transport is carried out by the charge transport medium (principally by the hydrazone compound of this invention), and is similar to the mechanism in the photoreceptor shown in FIG. 2. In this case (i.e., FIG. 3) also, the hydrazone compound exhibits a function as a charge transport substance.

In the photoreceptor of FIG. 4, the generation of charge takes place in the charge generating layer 5 upon exposure to light, and the charge transport layer 4 receives injection of the charge and transports it. The mechanism of the generation and the transport of charge, which are essential to the photo-induced discharge, is similar to those in the photoreceptors shown in FIGS. 2 and 3. In this case also, the hydrazone compound functions as a charge transport substance.

A photoreceptor according to FIG. 1 can be produced as follows: The hydrazone compound is dissolved in a solution of a binder, and a sensitizing dye is optionally added thereto. The resulting solution is coated on a conductive support 1 and dried.

A photoreceptor according to FIG. 2 can be obtained by dispersing fine grains of a charge generating substance in a solution of the hydrazone compound and a binder in a solvent, coating the resulting dispersion on a conductive support, and then drying it.

A photoreceptor according to FIG. 3 can be obtained by a method which includes the steps of: coating a charge generating substance by a vacuum evaporation process onto a conductive support, or coating a dispersion (which is prepared by dispersing fine grains of a charge generating substance into a solvent in which a binder is optionally dissolved) on a conductive support and drying the coat; finishing the surface of the vacuum evaporation coated layer or the dispersion coated layer using a technique such as buff rubbing; adjusting the layer thickness to a proper value, if necessary; and coating thereon a solution containing both the hydrazone compound and a binder and drying it. The coating steps can be carried out by usual means, such as doctor blade, wire bar, or so forth.

A photoreceptor according to FIG. 4 can be obtained by coating a solution containing the hydrazone compound and a binder on a conductive support using a known means, drying the coating, and then providing a charge generating layer in the same manner as in the photoreceptor of FIG. 3.

The thickness of the light-sensitive layer in FIGS. 1 and 2 each ranges from 3 to 50 $\mu$m, and preferably from 5 to 20 $\mu$m. In each of FIGS. 3 and 4, the thickness of the charge generating layer is less than 5 $\mu$m, and preferably less than 2 $\mu$m, and the thickness of the charge transport layer ranges from 3 to 50 $\mu$m, and preferably from 5 to 20 $\mu$m.

In the photoreceptor of FIG. 1, the amount of the hydrazone compound in the light-sensitive layer ranges from 30 to 70% by weight, and preferably about 50% by weight, based on the total weight of the light-sensitive layer. On the other hand, the amount of sensitizing dye added to the sensitive layer in order to confer sensitivity in the visible region ranges from 0.1 to 5% by weight, and preferably from 0.5 to 3% by weight, based on the total weight of the light-sensitive layer.

In the photoreceptor of FIG. 2, the amount of the hydrazone compound in the light-sensitive layer ranges from 10 to 95 wt%, and preferably from 30 to 90 wt%, and the amount of a charge generating substance is not more than 50 wt%, and preferably 20 wt% or less.

The amount of hydrazone compound contained in the charge transport layer in the photoreceptor of FIG. 3 or 4 is, by analogy with in the light-sensitive layer of the photoreceptor shown in FIG. 2, from 10 to 95 wt%, and preferably from 30 to 90 wt%.

Plasticizers can be employed together with a binder in producing any of the photoreceptors shown in FIGS. 1 to 4.

In the photoreceptors of this invention, a plate or a foil of a metal (such as aluminum), a plastic film onto which a conductive metal (e.g., aluminum) is vacuum evaporated, paper which has received a conductivity providing treatment, or so on, can be used as a conductive support. As a binder, not only condensed resins such as polyamide, polyurethane, polyester, epoxy resin, polyketone, polycarbonate, etc., and vinyl polymers such a polyvinyl ketone, polystyrene, poly-N-vinylcarbazole, polyacrylamide, etc., but also all resins possessing both insulting and adhesive properties can be used.

As a plasticizer, halogenated paraffins, polychlorobiphenyl, dimethylnaphthalene, dibutyl phthalate, and so on can be employed.

Examples of a sensitizing dye that can be employed in the photoreceptor of FIG. 1 include triarylmethane dyes such as Brilliant Green, Victoria Blue B, Methyl Violet, Crystal Violet, Acid Violet 6B, etc.; xanthene dyes such as Rhodamine B, Rhodamine 6G, Rhodamine G Extra, Eosine S, Erythrosine, Rose Bengale, Fluoresceine, etc.; thiazine dyes such as Methylene Blue; cyanine dyes such as cyanine; pyrylium dyes such as thiapyrylium perchlorate, a benzopyrylium salt (as described in published examined Japanese Patent Application No. 25658/73, etc.); and so on.

Examples of a charge generating substance employable in the photoreceptors shown in FIGS. 2 to 4 include inorganic pigments such as selenium, Se-Te, CdS, CdS-Se and the like; and organic pigments such as azo series dyes (e.g., CI Pigment Blue 25 (CI21180), CI Pigment Red 41 (CI21200), CI Acid Red 52 (CI45100), CI Basic Red 3 (CI45210), etc.), phthalocyanine series dyes (CI Pigment Blue 16 (CI74100), etc.), indigo series dyes (e.g., CI Vat Brown 5 (CI73410), CI Vat Dye (CI73030), etc.), perylene series dyes (e.g., Algol Scarlet B (produced by Bayer Co.), Indanthrene Scarlet R (produced by Bayer Co.), etc.) and so on.

In addition, amorphous silicon as described in Japanese Patent Application (OPI) Nos. 86341/79, 116930/79, 145537/79 and so on can be also employed as the charge generating substance.

Furthermore, in the photoreceptor produced in the above-described manner, an adhesion layer or a barrier layer may be optionally provided between the conductive support and the light-sensitive layer. Materials employed for such layers include polyamide, nitrocellulose, aluminum oxide and so on, and a preferable thickness thereof is 1 μm or less.

A process for carrying out copying using the photoreceptor of this invention includes the steps of charging the surface of the photoreceptor, exposing the charged surface to a pattern of light, developing latent image thus formed, and optionally transferring the developed image onto plain paper or the like.

The photoreceptors of this invention have advantages in that their stability to light and heat are significantly improved and dark decay is reduced to a great extent.

In order to investigate stability to light, the hydrazone compounds (Compound (1) and Compound (3)) and N-alkylamino substituted hydrazone compounds (represented by the following structural formulae (a) and (b)), employed for comparison, respectively, were dissolved in dichloromethane solutions in the same concentration of $10^{-4}$ mol/l:

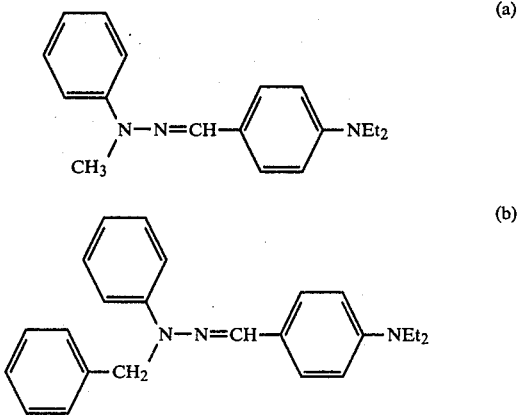

Next, each of the solutions was irradiated with ultraviolet rays, and the absorption spectrum of the irradiated solution was measured at regular time intervals.

Figure 5:
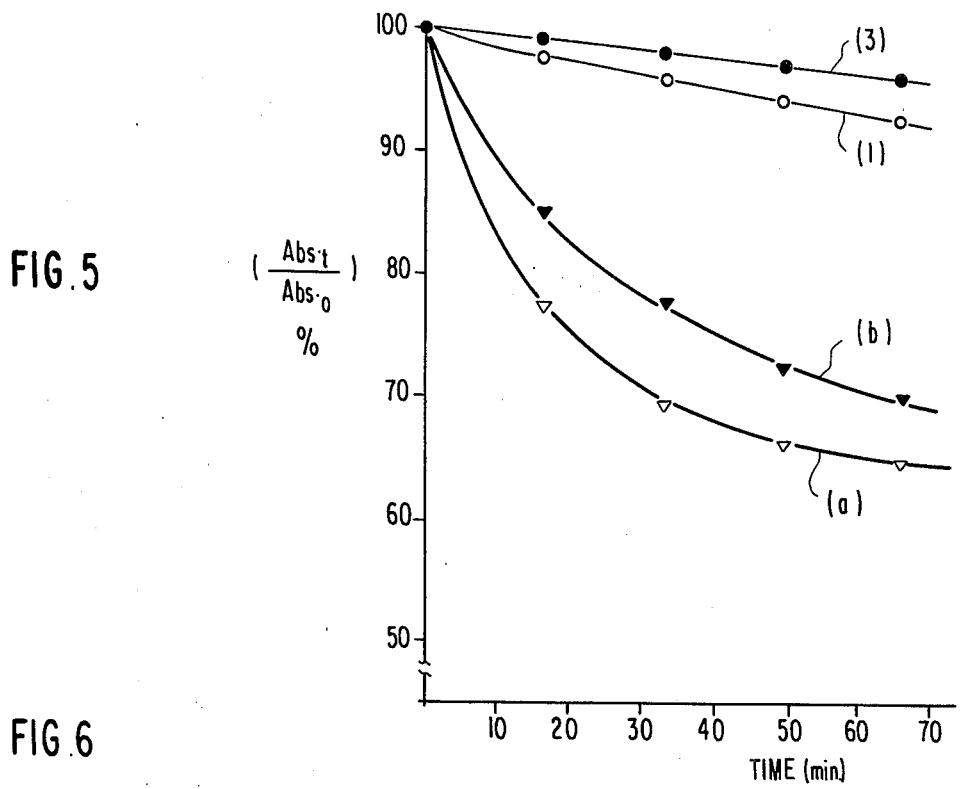
FIG. 5 is a graph illustrating the stabilities to light of N-arylamino substituted compounds of this invention and those of N-alkylamino substituted compounds for comparison.

The results are shown in FIG. 5. Therein, the numbers on the ordinate indicate the ratio of absorbance at the wavelength where the compound to be investigated exhibits its absorption maximum (which is 374 nm in the cases of the hydrazone compounds of this invention (1) and (3), and 359 nm in the cases of N-alkylamino substituted compounds (a) and (b) employed for comparison) before irradiation with ultraviolet rays, which absorbance is represented by $Abs_o$, to absorbance at the same wavelength after t minutes' irradiation, which absorbance is represented by $Abs_t$, calculated in terms of percentages, that is $(Abs_t/Abs_o) \times 100$; that is, the degree of reduction in the absorbance at the wavelength exhibiting the absorption maximum is plotted as the ordinate, and irradiation time is plotted as the abscissa.

It is apparent from FIG. 5 that when the N-arylamino substituted compounds are used in place of the N-alkylamino substituted compounds the stability to light is significantly improved.

In accordance with embodiments of this invention, photoreceptors are obtained which have very high sensitivity, reduced residual potential (if the residual potential is high, fog will be caused in copies obtained), reduced variations in the residual potential and the sensitivity even when used repeatedly a number of times, and excellent durability.

This invention will now be illustrated in greater detail by reference to the following examples. However, the invention is not intended to be construed as being limited to these examples. Unless otherwise indicated, all parts are by weight.

EXAMPLE 1

A charge generating layer was formed by vacuum evaporation coating of selenium in a layer of 0.4 μm thickness onto a grained aluminum plate having a thickness of about 300 μm. Thereon, a solution prepared by dissolving 4 parts of the hydrazone compound (1) and 5 parts of polycarbonate of bisphenol A (trademarked Lexan-121, produced by General Electric Co.) in 130 parts of dichloromethane was coated using a wire wound rod, and dried to result in formation of a charge transport layer having a thickness of about 5 μm. Thus, an electrophotographic photoreceptor having a light-sensitive layer constituting two layers was obtained.

A negative potential of −5 kv was created on the surface of the thus obtained photoreceptor using a corona discharge device, that it, an electrostatic copying paper testing apparatus (SP-428 model, produced by Kawaguchi Electric Mfg. Co., Ltd.) and then, the surface was exposed to light generated from a 3,000° K. of tungsten lamp under such conditions that the intensity of illumination at the surface was 10 lux. The exposure was continued till the surface potential was reduced to half the initial potential, and from the time for such reduction, half decay exposure $E_{50}$ (lux·sec) was calculated.

The result was $E_{50}=9.5$·lux sec.

The value of $E_{50}$ determined after the charging-exposure process was repeated 3,000 times was 9.9 lux·sex, and these results revealed that variation in sensitivity was very small.

EXAMPLES 2 TO 4

Photoreceptors No. 2, No. 3 and No. 4 were produced in the same manner as in Example 1 except that the hydrazone compounds (3), (9) and (10), respectively, were used in place of the charge transport substance used in Example 1.

The $E_{50}$ value of each of these photoreceptors was determined in the same manner as in Example 1. The results are shown in the following table.

| Photoreceptor | $E_{50}$ (lux · sec) |
|---|---|
| No. 2 | 11.0 |
| No. 3 | 8.9 |
| No. 4 | 10.3 |

EXAMPLE 5

A coating solution was prepared as follows: 5 parts of β-type copper phthalocyanine was added to 660 parts of dichloromethane and dispersed thereinto using supersonic waves. To the thus prepared dispersion was added 40 parts of polycarbonate of bisphenol A (Lexan-121, trademark) and 40 parts of the hydrazone compound (1), and they were dissolved in the dispersion. The thus obtained coating solution was coated on a conductive transparent support (which had a vacuum evaporation coating film of indium oxide on a polyethylene terephthalate film support having a thickness of 100 μm, and exhibited a surface resistance of $10^3$ Ω) using a wire wound rod, and then dried. Thus, a light-sensitive layer having a thickness of about 10 μm was obtained.

After positive potential was created on this photoreceptor by +5 kv of corona discharge, sensitivity of this photoreceptor was determined in the same manner as in Example 1. The value of $E_{50}$ in this case was 10.4 lux·sec.

EXAMPLES 6 TO 12

Photoreceptors No. 6, No. 7, No. 8, No. 9, No. 10, No. 11 and No. 12 were produced in the same manner as in Example 5 except that the hydrazone compounds (3), (4), (5), (6), (12), (18) and (19), respectively, were employed instead of the charge transport substance used in Example 5.

The $E_{50}$ value of each of these photoreceptors was determined in the same manner as in Example 5. The results obtained are shown in the following table.

| Photoreceptor | $E_{50}$ (lux · sec) |
|---|---|
| No. 6 | 18.6 |
| No. 7 | 19.5 |
| No. 8 | 9.0 |
| No. 9 | 11.2 |
| No. 10 | 19.2 |
| No. 11 | 10.5 |
| No. 12 | 9.7 |

EXAMPLE 13

Two parts of Chloro-Dian Blue (represented by the following structural formula (c)) and the same parts of polycarbonate of bisphenol A (Lexan-121) were added to 260 parts of dichloromethane, and ground to powder and mixed with each other in a ball mill. Thus, a charge generating pigment dispersion was prepared.

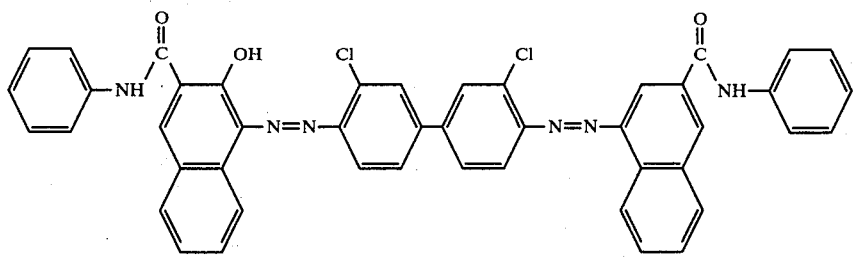

(c)

The thus prepared dispersion was coated on a conductive transparent support (which had a vacuum evaporation coated film of indium oxide on a polyethylene terephthalate support having a thickness of 100 μm, and exhibited a surface resistance of $10^3$ Ω) using a wire wound rod, and dried the coat to result in the formation of a charge generating layer about 1 μm thick.

Next, a solution dissolving 2 parts of the hydrazone compound (1) and 4 parts of polycarbonate of bisphenol A (Lexan-121) in 60 parts of dichloromethane was coated on the charge generating layer using a wire wound rod and then dried the coat to result in the formation of a charge transport layer having a thickness of about 8 μm.

The value $E_{50}$ of the photoreceptor having the light-sensitive layer which the thus obtained two layers constituted was determined in the same manner as in Example 1. The result was 5.0 lux·sec.

EXAMPLES 14 TO 16

Photoreceptors No. 14, No. 15 and No. 16 were produced in the same manner as in Example 13 except that the hydrazone compounds (3), (5) and (18), respectively, were employed instead of the charge transport substance used in Example 13.

The $E_{50}$ value of each of these photoreceptors was determined in the same manner as in Example 13. The results obbtained are set forth in the following table.

| Photoreceptor | $E_{50}$ (lux · sec) |
| --- | --- |
| No. 14 | 6.4 |
| No. 15 | 5.1 |
| No. 16 | 5.8 |

EXAMPLE 17

A photoreceptor No. 17 was produced in the same manner as in Example 5 except that the N-alkylamino substituted compound represented by the structural formula (a) was employed for comparison instead of the hydrazone compound (1).

A positive potential was created by +5 kv of corona discharge on the surface of the photoreceptor obtained in Example 5 and the above-described photoreceptor No. 17, and thereafter each of the two photoreceptors was examined in the decay of surface potential in the dark.

Figure 6:
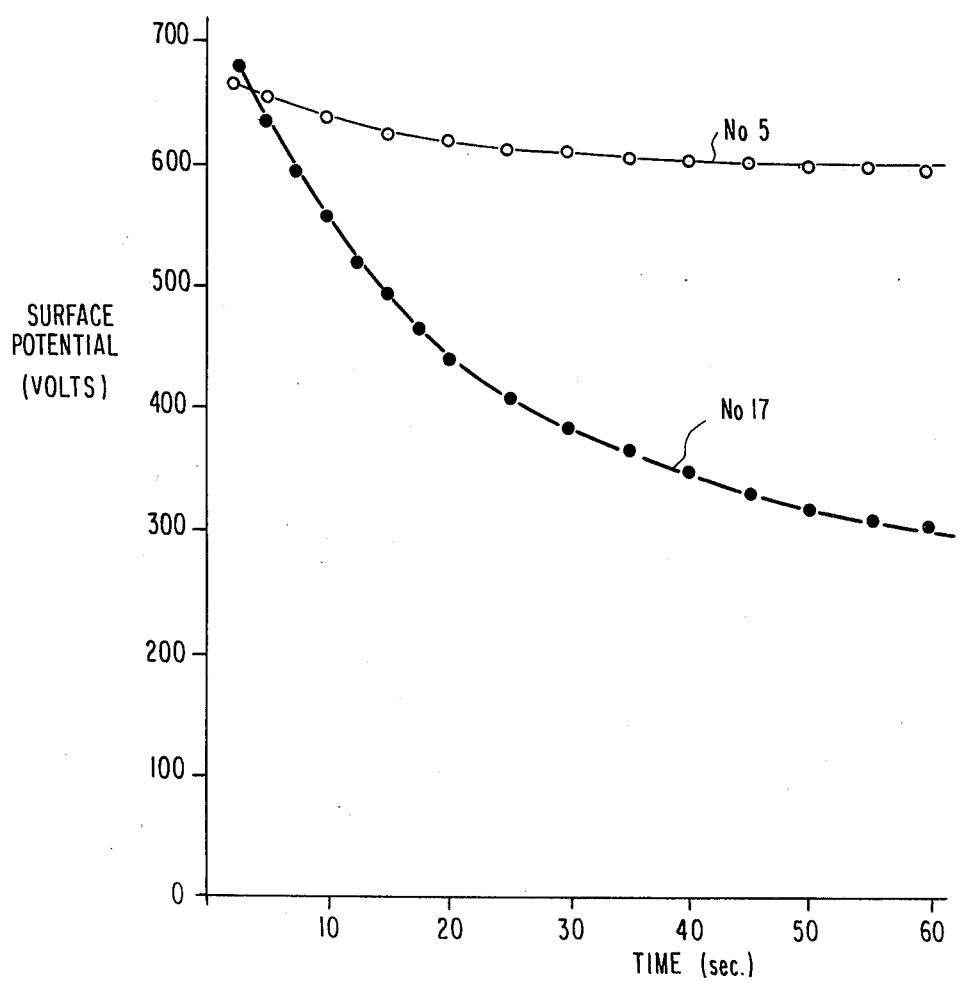
FIG. 6 is a graphical representation of the dark decay of surface potential created by charging the surfaces of photoreceptors utilizing N-arylamino substituted compounds of this invention and an N-alkylamino substituted compound for comparison, respectively.

In FIG. 6, when the results are plotted, with surface potential as ordinate and passage of time after charging as abscissa, dark decay curves are obtained.

It is apparent from FIG. 6 that the dark decay characteristics are greatly improved by the use of the N-arylamino substituted compound instead of the N-alkylamino substituted compound.

While the invention has been described in detail and with reference to specific embodiments thereof, it will be apparent to one skilled in the art that various changes and modifications can be made therein without departing from the spirit and scope thereof.

What is claimed is:

1. An electrophotographic photoreceptor comprising a conductive support with a light-sensitive layer thereon containing a hydrazone compound represented by formula (I) or, (II):

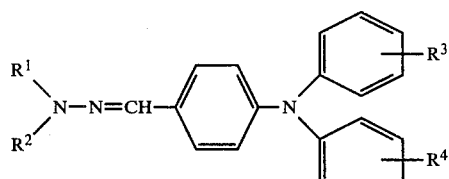

(I)

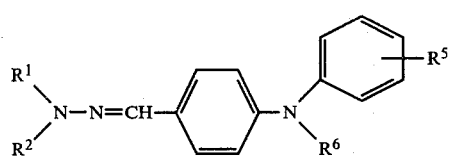

(II)

wherein X represents O, S or >N—$R^6$; $R^1$ and $R^2$ each represents a non-substituted or a substituted straight or branched chain alkyl group containing from 1 to 12 carbon atoms, a non-substituted or a substituted straight or branched chain aralkyl group containing from 7 to 20 carbon atoms, or a non-substituted or a substituted aryl group, the aryl group including monovalent residues of monocyclic aromatic rings and condensed polycyclic aromatic rings having from 2 to 4 rings therein; $R^3$, $R^4$ and $R^5$ each represents hydrogen, a non-substituted or a substituted straight or branched chain alkyl group containing from 1 to 12 carbon atoms, a non-substituted or a substituted straight or branched chain aralkyl group containing from 7 to 20 carbon atoms, a straight or a branched chain alkoxy group containing from 1 to 4 carbon atoms, an aryloxy group containing from 6 to 10 carbon atoms, an acyl group containing from 2 to 8 carbon atoms, and alkoxycarbonyl group containing from 2 to 5 carbon atoms, a halogen atom, a nitro group, a monoalkylamino group whose alkyl moiety contains from 1 to 4 carbon atoms, a dialkylamino group whose alkyl moiety contains from 1 to 4 carbon atoms, or an amido group containing from 2 to 8 carbon atoms; and $R^6$ represents a non-substituted or a substituted straight or branched chain alkyl group containing from 1 to 12 carbon atoms, or a non-substituted or a substituted straight or branched chain aralkyl group containing from 1 to 12 carbon atoms.

2. An electrophotographic photoreceptor as in claim 1, wherein at least one of the groups represented by $R^1$ through $R^6$ has a substituent group, and the substituent group is selected from a halogen atom, an alkoxy group, an aryloxy group, a dialkylamino group, and an alkylthio group.

3. An electrophotographic photoreceptor as in claim 1, wherein at least one of the groups represented by $R^1$ through $R^6$ is an aryl group which has a substituent group, and the substituent group is selected from a halogen atom, an alkoxy group, an aryloxy group, a dialkylamino group, an alkylthio group, and an alkyl group.

4. An electrophotographic photoreceptor as in claim 1, 2, or 3, wherein said light-sensitive layer is formed of (1) a charge transport medium comprising said hydrazone compound and a binder, and (2) a charge generating substance dispersed in said charge transport medium.

5. An electrophotographic photoreceptor as in claim 1, 2, or 3, wherein said light-sensitive layer is formed of (1) a charge transport layer containing said hydrazone compound and (2) a charge generating layer.

6. An electrophotographic photoreceptor as in claim 1, wherein the amount of said hydrazone compound in said light-sensitive layer ranges from 30% to 70% by weight, based on the total weight of said light-sensitive layer.

7. An electrophotographic photoreceptor as in claim 1, wherein said light-sensitive layer contains a sensitizing dye in an amount of from 0.1% to 5% by weight, based on the total weight of said light-sensitive layer.

8. An electrophotographic photoreceptor as in claim 4, wherein said light-sensitive layer contains 10 to 95 wt% of the hydrazone compound and 50 wt% or less of the charge generating substance.

9. An electrophotographic photoreceptor as in claim 5, wherein the amount of said hydrazone compound in said charge transport layer ranges from 10 wt% to 95 wt%, based on the total weight of said charge transport layer.

10. An electrophotographic photoreceptor as in claim 1 wherein said light-sensitive layer comprises said hydrazone compound and a binder.

* * * * *